United States Patent
Kim et al.

(10) Patent No.: US 7,202,324 B2
(45) Date of Patent: Apr. 10, 2007

(54) PERFLUOROSTYRENE COMPOUND, AND COATING SOLUTION AND OPTICAL WAVEGUIDE DEVICE USING THE SAME

(75) Inventors: Ji-Hyang Kim, Daejeon (KR); Jae-Il Kim, Daejeon (KR); Tae-Kyun Kim, Daejeon (KR); Hyung Jong Lee, Daejeon (KR); Seon Gyu Han, Daejeon (KR)

(73) Assignee: Chemoptics Inc., Daejeon (KR)

( * ) Notice: Subject to any disclaimer, the term of this patent is extended or adjusted under 35 U.S.C. 154(b) by 27 days.

(21) Appl. No.: 11/034,646

(22) Filed: Jan. 13, 2005

(65) Prior Publication Data

US 2005/0163451 A1 Jul. 28, 2005

Related U.S. Application Data

(63) Continuation of application No. 10/616,889, filed on Jul. 10, 2003, now abandoned.

(30) Foreign Application Priority Data

Jul. 12, 2002 (KR) ............ 10-2002-0040901

(51) Int. Cl.
*C08G 65/40* (2006.01)

(52) U.S. Cl. ............ 528/219; 528/125; 528/128; 528/171; 528/174; 528/205; 524/544; 570/206; 570/140

(58) Field of Classification Search ............ 528/219, 528/125, 128, 171, 174, 205
See application file for complete search history.

(56) References Cited

U.S. PATENT DOCUMENTS 5,115,082 A * 5/1992 Mercer et al. ............ 528/219

(Continued)

FOREIGN PATENT DOCUMENTS

KR 100226442 B1 7/1999

OTHER PUBLICATIONS

Ding et al. J. Polym. Sci.,: Part A: Polym. Chem., vol. 40, pp. 4205-4216, (2002). Wiley Inc. accepted on Aug. 29, 2002.*

(Continued)

*Primary Examiner*—David W. Wu
*Assistant Examiner*—Henry S. Hu
(74) *Attorney, Agent, or Firm*—The Webb Law Firm

(57) ABSTRACT

Disclosed is a fluorine compound having perfluorostyrene introduced at a terminal thereof, as represented in the following Formula 1, and a coating solution and an optical waveguide device using the same, characterized in that the introduction of perfluorostyrene results in a facile fabrication of thin films by a UV curing or a thermal curing, high thermal stability and chemical resistance, and low optical propagation loss and birefringence:

Formula 1

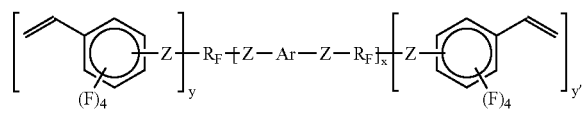

Wherein Z is O or S; $R_F$ is an aliphatic or aromatic group; y is a natural number of 1–10; y' is an integer of 0–1; x is an integer of 0–200; and

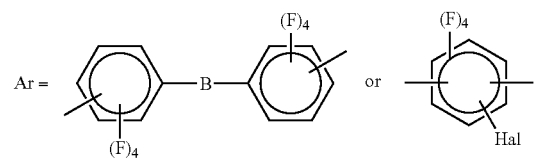

Wherein B is a single bond or selected from the group consisting of —CO—, —SO$_2$—, —S— and —O—, and Hal is selected from the group consisting of F, Cl, Br and I.

6 Claims, 2 Drawing Sheets

U.S. PATENT DOCUMENTS

| | | | |
|---|---|---|---|
| 5,438,142 | A | 8/1995 | Fritsch et al. |
| 5,598,501 | A | 1/1997 | Maruo et al. |
| 6,002,828 | A * | 12/1999 | Hult et al. .................. 385/141 |
| 6,235,353 | B1 * | 5/2001 | Drage et al. ................ 427/493 |
| 6,306,563 | B1 | 10/2001 | Xu et al. |
| 6,323,301 | B1 * | 11/2001 | Smith et al. ................ 528/125 |

OTHER PUBLICATIONS

Liu et al., "Preparation of Highly Fluorinated Poly(ether sulfone)s under Mild Polycondensation Conditions Using Molecular Sieves", Macromol. Rapid Commun., vol. 23, pp. 844-848, (Oct., 2002).*

Ding et al., "Fluorinated Poly(arlene ether ketone)s Bearing Pentafluorostyrene Moieties Prepared by a Modified Polycondensation", Journal of Polymer Science: Part A: Polymer Chemistry, vol. 40-4205-4216 (Aug. 29, 2002).

Eldada et al., "Advances in Polymer Integrated Optics" IEEE Journal of Selected Topics in Quantum Electronics, vol. 6, No. 1. pp. 54-68, Jan./Feb. 2000.

Matsuura et al. "Polymides Derived from 2,2'—Bis (trifluoromethl)—4,4'—diaminaobiphenyl. 4. Optical Properties of Fluorinated Polymides for Optoelectronic Components"; Macromolecules, vol. 27, pp. 665-6670, 1994.

Matsuura et al. "Low Loss, Heat-Resistant Optical Waveguides Using New Fluorinated Polymides"; Electronic Letters, vol. 29, No. 3 pp. 269-271, Feb. 4, 1993.

* cited by examiner

[Figure 1]
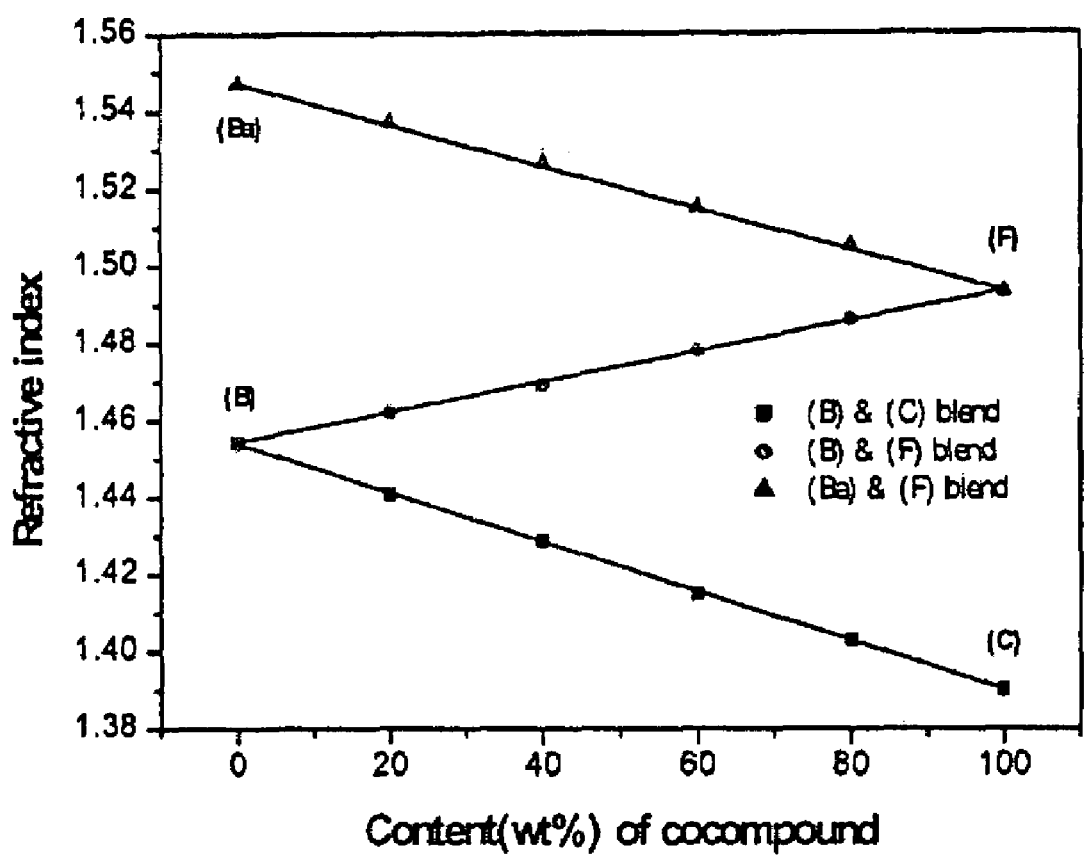

[Figure 2]
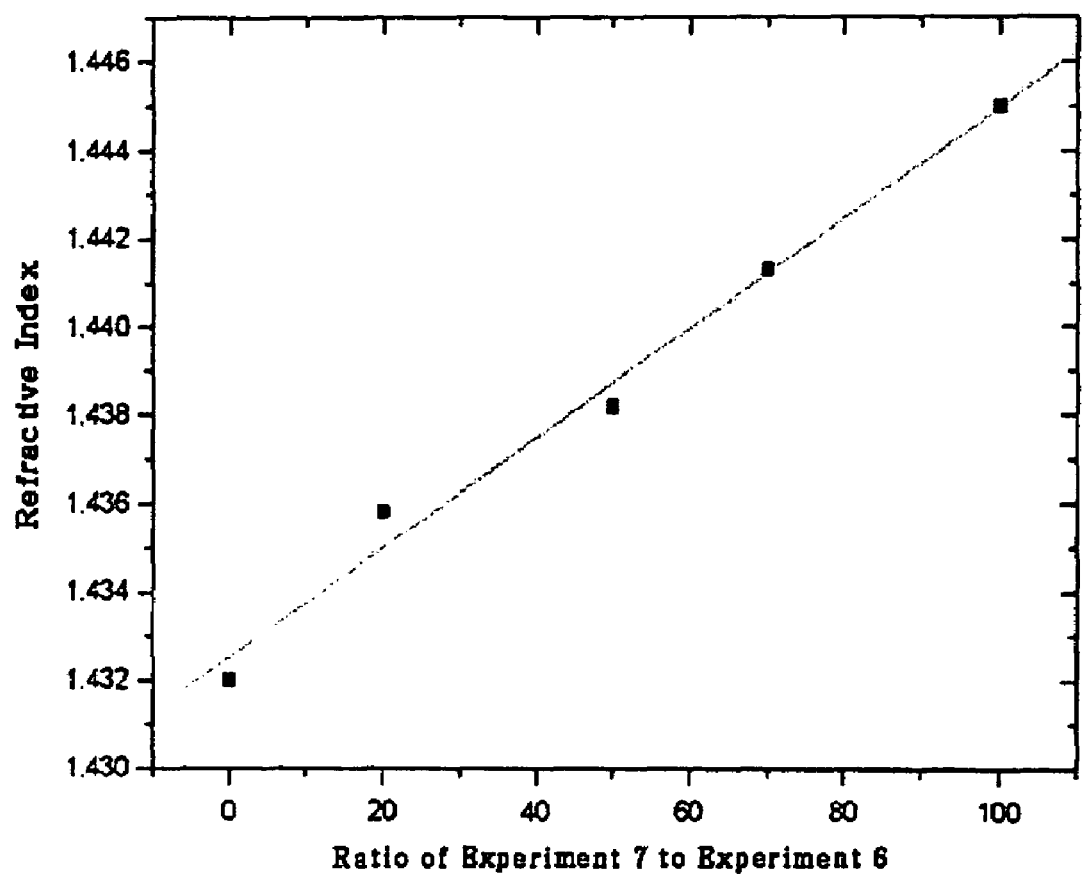

PERFLUOROSTYRENE COMPOUND, AND COATING SOLUTION AND OPTICAL WAVEGUIDE DEVICE USING THE SAME

BACKGROUND OF THE INVENTION

1. Field of the Invention

The present invention relates, in general, to perfluorostyrene compounds, and coating solutions and optical waveguide devices using the same. In particular, the present invention is directed to a fluorine compound having perfluorostyrene moiety, and a coating solution and an optical waveguide device using the same. These fluorinated compounds are applied for a core and a cladding material of various planar optical waveguide devices, such as optical switches, variable optical attenuators (VOA), tunable and fixed wavelength filters, arrayed waveguide grating (AWG) devices, etc.

2. Description of the Related Art

Generally, polymeric optical waveguide devices should be required the reliability based on Telcodia test for the optical communication network. In such a case, the polymer material should have very high thermal stability and environmental stability. Further, there are required accurate control of a refractive index and low birefringence as well as low optical propagation loss at a telecommunication wavelength region. Furthermore, in order to fabricate a desirable optical device, the polymer material should have excellent adhesion to any substrate. Of the above-mentioned requirements, the optical propagation loss and the birefringence are regarded as very important characteristics. The optical propagation loss on a polymer thin film is mainly caused by the light absorption by a harmonic overtone vibration mode of a C—H bond in the presence of polymer. Such light absorption at wavelengths of near far infrared can be decreased by substituting deuterium (D) or halogen elements, such as fluorine (F), for hydrogen of C—H bond (or O—H, N—H), whereby an absorption wavelength band can be shifted to 5–25 μm. Therefore, the loss can be lowered at communication wavelengths.

On the other hand, the birefringence of the thin film is caused by a molecular structure and a stress of a thin film-preparing process.

Accordingly, various polymer materials have been developed to meet all the requirements. In this regard, a fluorinated polyimide compound, which is known to have excellent heat resistance, even at about 400° C., has been continuously applied for optical waveguide devices (U.S. Pat. No. 5,598,501, Macromolecules, vol 27, pp 6665, 1994 and Electronics Letters, 29(3) 269, 1993). However, polyimide suffers from drawbacks, such as relatively high optical loss of 0.7 dB/cm or more and a high birefringence of 0.008 or more.

As another polymer material, there is proposed UV-curable fluorinated acrylate including various compositions, which is advantageous in terms of relatively low optical loss of 0.3 dB/cm at 1.55 μm and a birefringence of 0.0008. (U.S. Pat. No. 6,306,563 B1, and IEEE Journal of selected topics in quantum electronics vol. 6, pp 54, 2000).

As still another polymer material, there is proposed fluorinated polyarylene ether having a low dielectric constant, and excellent mechanical strength and processability (U.S. Pat. No. 5,115,082), which shows the possibility as a potential optical polymer. In addition, the above polymer system is added with a thermally curable reactive group, to drastically increase chemical resistance, whereby such a polymer is applied for the optical waveguide device (Korean Patent No. 226,442). Consequently, fluorinated polyarylene ether based polymers have been further improved in optical loss (0.4 dB/cm) and birefringence (0.004), compared to polyamide-based polymers, but is disadvantageous of still high birefringence and high processing temperatures (280° C. or more).

SUMMARY OF THE INVENTION

To avoid the problems encountered in the related art, perfluorostyrene is introduced at a terminal of a compound for use in an optical device, whereby inherent light absorption caused by a higher order harmonic vibration mode of a C—H bond in the compound can be prevented in optical communication wavelength, thus realizing low optical loss, low optical birefringence, precise control of a refractive index, and a fabrication of optical devices at low temperatures in a short process time.

Therefore, it is the object of the present invention to provide a fluorinated compound having perfluorostyrene introduced at a terminal thereof.

Another object of the present invention is to provide a coating solution using the fluorinated compound.

Still another object of the present invention is to provide an optical waveguide device using the fluorinated compound.

BRIEF DESCRIPTION OF THE DRAWINGS

The above and other objects, features and other advantages of the present invention will be better understood from the following detailed description taken in conjunction with the accompanying drawings, in which:

FIG. 1 shows the refractive index according to blending ratio of fluorinated compounds of the present invention; and FIG. 2 shows the precise control of refractive index according to blending ratio of coating solutions of the present invention.

DETAILED DESCRIPTION OF THE INVENTION

Based on the present invention, a fluorinated compound having perfluorostyrene introduced at a terminal thereof is synthesized through a reaction of polyol and pentafluorostyrene, which is represented by the following Formula 1:

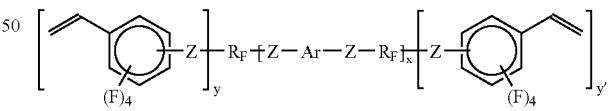

Formula 1

Wherein Z is O or S; $R_F$ is an aliphatic or aromatic group; y is a natural number of 1–10; y' is an integer of 0–1; x is an integer of 0–200; and

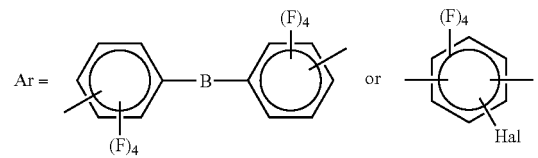

Wherein B is a single bond or selected from the group consisting of —CO—, —SO$_2$—, —S— and —O—; and Hal is selected from the group consisting of F, Cl, Br and I.

Preferably, the fluorinated polymer compound having perfluorostyrene introduced at a terminal thereof is represented by the following. Formula 2 in which y and y' are 1:

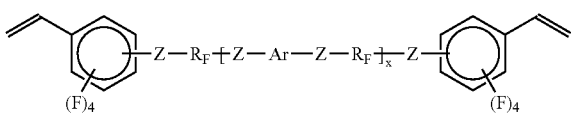

Formula 2

Wherein Z is O or S, preferably O, and preferred R$_F$ is —CH$_2$(CF$_2$)$_n$CH$_2$—, —CH$_2$CF$_2$O(CF$_2$CF$_2$O)$_n$CF$_2$CH$_2$—, or

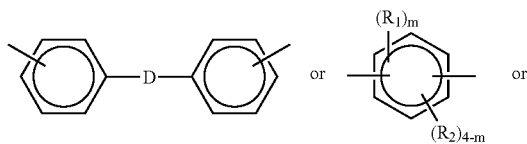

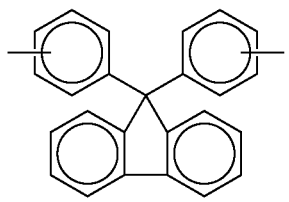

Wherein x is an integer of 0–200, and preferably 2–50; D is selected from the group consisting of —C(CF$_3$)$_2$—, —C(CH$_3$)$_2$—, —CO—, —SO$_2$—, —O— and —S—; R$_1$ and R$_2$ are independently selected from the group consisting of H, or halogen elements, such as F, Cl, Br and I; and m is a natural number of 1–3.

Represented by Formula 2 in which Z is O; x is an integer of 2–50; Ar is halogenated pentafluorobenzene; and R$_F$ is —CH$_2$(CF$_2$)$_n$CH$_2$—, —CH$_2$CF$_2$(OCF$_2$CF$_2$)$_n$OCF$_2$CH$_2$— or

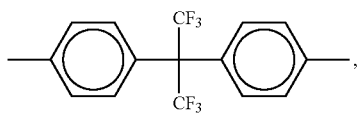

the perfluorostyrene-introduced fluorine compound can be synthesized.

In case where x and y' are 0 in Formula 1, the perfluorostyrene-introduced fluorine compound is represented by the following Formula 3:

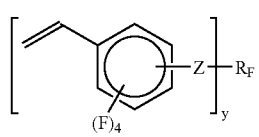

Formula 3

Wherein R$_F$ is an aliphatic or aromatic compound, and y is a natural number of 1–10. Preferably, Z is O, and R$_F$ is a substituted or unsubstituted alkyl group when y is 1, and R$_F$ is the same as RF of Formula 2 when y is 2.

In addition, the fluorine compound having perfluorostyrene introduced at a terminal thereof can be synthesized, as represented by Formula 3 in which R$_F$ is —CH$_2$ (CF$_2$)$_n$ CH$_2$—, —CH$_2$CF$_2$ (OCF$_2$CF$_2$)$_n$OCF$_2$CH$_2$—, or

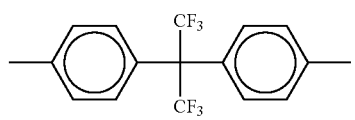

when y is 2.

Further, the fluorine compound having perfluorostyrene introduced at a terminal thereof can be synthesized, as represented by Formula 3 in which when y is 3, R$_F$ is an aromatic or aliphatic group, and more preferably, R$_F$ = 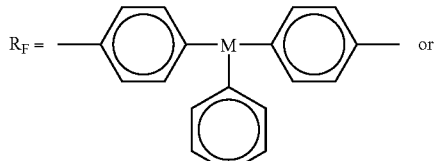 or

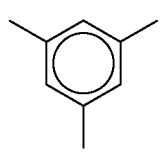

Wherein M is selected from the group consisting of C—CH$_3$, C—CF$_3$, C—CCl$_3$, and C—CBr$_3$, or selected from the group consisting of N, P and P═O.

Furthermore, it is possible to synthesize the perfluorostyrene-introduced fluorine compound as represented by Formula 3 in which —Z—R$_F$ is an aromatic or aliphatic polyol when y is 4 or more.

The fluorine compound represented by Formula 2 can be synthesized by reaction of an aliphatic or aromatic diol and a fluorinated aromatic compound in the presence of a base such as NaOH or K$_2$CO$_3$ in DMAc (dimetylacetamide). The reaction mixture was stirred at room temperature for ambient hours. And then to this mixture, pentafluorostyrene was added and stirred for more hours for complete reaction.

Below, Formula 4 shows representative the polymers having perfluorostyrene introduced at a terminal thereof. In addition to the chemical structures shown in Formula 4, derivatives substituted at a para-position through the above reaction may be produced with any amounts. Such derivatives are used without additional separation, to control the refractive index of an optical waveguide. In Formula 4, 'a' as a repeat unit number is preferably 2–50.

Formula 4
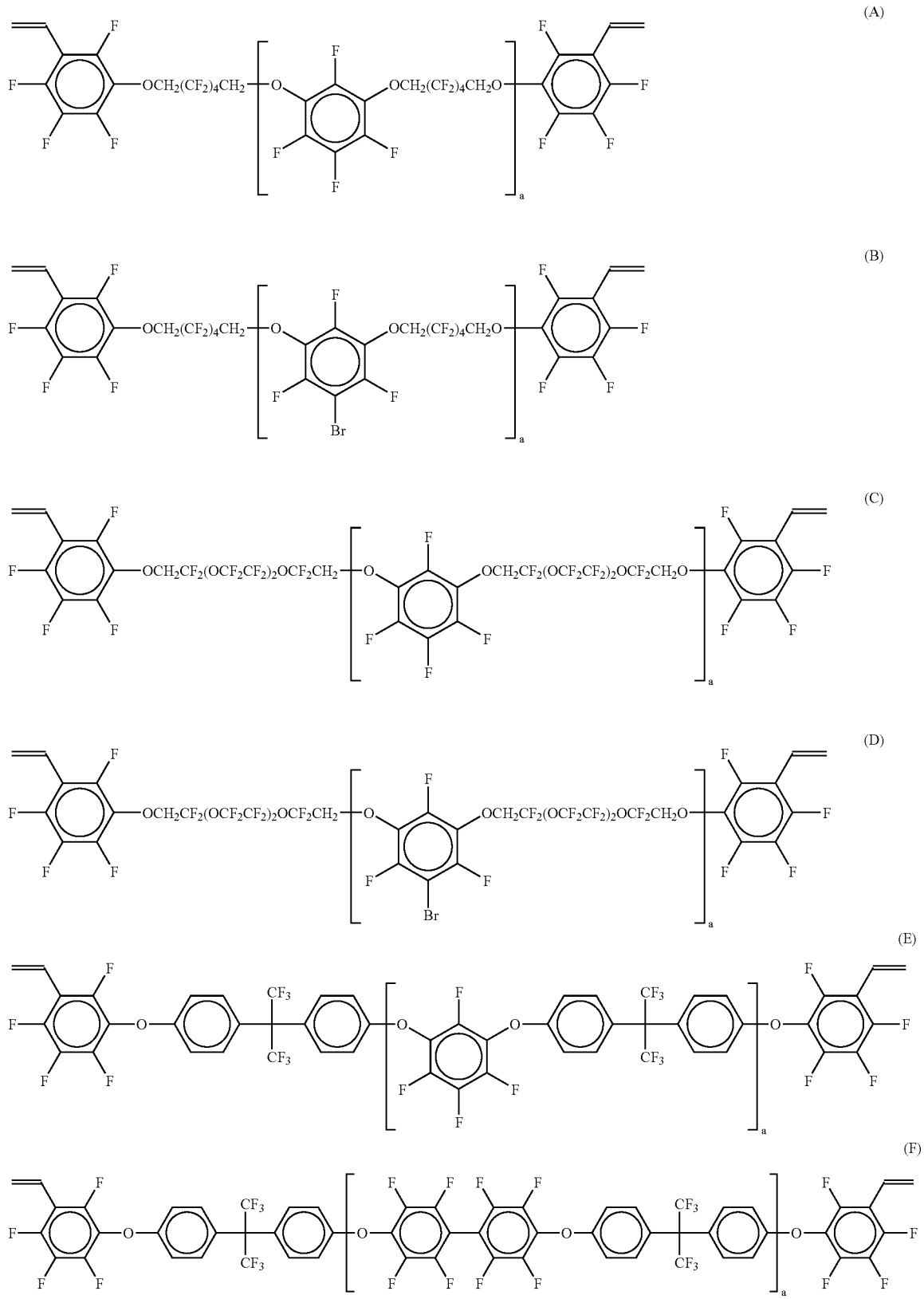

In addition, the compound represented by Formula 3 can be prepared by the reaction of selected from alcohol-containing $R_F$, preferably diol or triol, and pentafluorostyrene in the presence of a base such as $NaOH_1$ or $K_2CO_3$ in DMAc (dimethylacetamide).

Thereby, the representative fluorinated compounds having perfluorostyrene introduced at a terminal thereof are obtained, as represented by the following Formulas 5 and 6. In addition to the chemical structures shown in Formulas 5 and 6, derivatives substituted at a para-position through the above reaction may be produced with any amounts. As such, the derivatives are used without additional separation for the control of a refractive index and curing characteristics of an optical waveguide device. Below, the compounds represented by Formula 5 are ones in which y is 2 in Formula 3, and the compounds represented by Formula 6 are ones in which y is 3 in Formula 3:

Formula 5

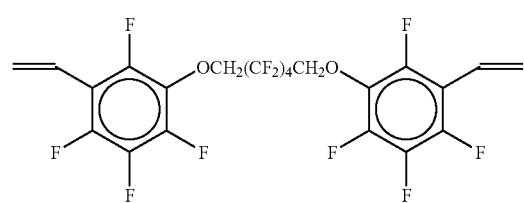
(Aa)

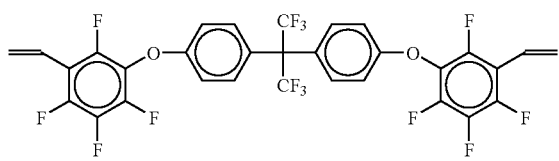
(Ab)

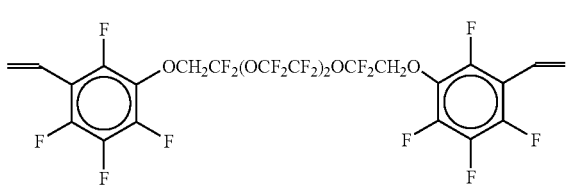
(Ac)

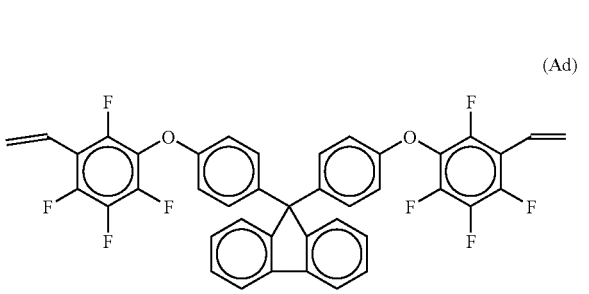
(Ad)

Formula 6

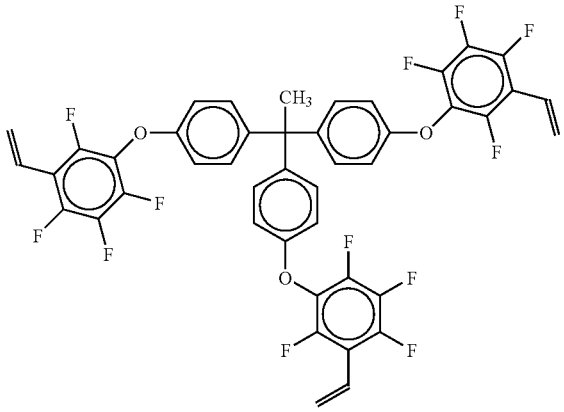
(Ba)

(Bb)

Meanwhile, a polymer material for application of optical waveguide device is used as a mixture comprising the fluorine compound having perfluorostyrene introduced at a terminal thereof, as represented by Formula 2 or 3, a photoinitiator and a reactive fluorinated acrylate compound represented by the following Formula 7, so as to control the refractive index and viscosity.

In such a case, the photoinitiator is not particularly limited so long as it can initiate a reaction of a styrene group, which is exemplified by Irgacure 184 Irgacure 651, etc., sold by CIBA GEIGY:

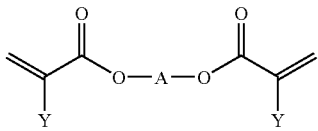
Formula 7

Wherein A is a fluorinated aliphatic or aromatic group, and Y is H or $CH_3$.

In particular, it is preferred that A is $-CH_2(CF_2)_nCH_2-$, $-CH_2CF_2(OCF_2CF_2)_nOCF_2CH_2-$ or

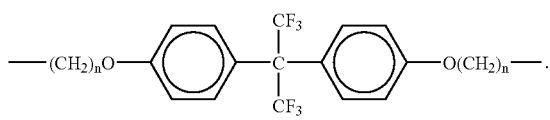

The compound represented by Formula 7 is obtained by the reaction of a fluorinated diol with acryloyl chloride in the presence of triethylamine. Synthesized acrylate compounds are represented by the following Formula 8:

Formula 8

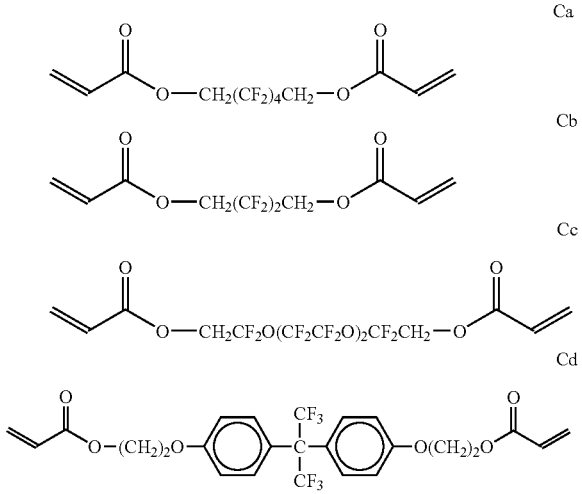

Further, with the aim of achieving a desired curing density, a formation of multi-layered thin films and a high adhesion to a substrate, a polymer material suitable for application in the optical waveguide device can be used as a mixture of the fluorine compound represented by Formula 1, the photoinitiator and the acrylate compound represented by Formula 7 or commercially available acrylate compound, such as 1,6-hexanediol diacrylate, tris(2-hydroxy ethyl)isocyanurate triacrylate, and pentaerythrol triacrylate.

More particularly, as for a coating solution for use in the formation of a core layer and a cladding layer in the optical waveguide device, at least one fluorine compound represented by Formula 1 is mixed with the photoinitiator and the compound of Formula 7 or the reactive compound and solvents are added as necessary. To produce a coating solution, perfluorostyrene introduced at a terminal thereof dissolved in propylene glycol methyl ether acetate (PG-MEA) or cyclohexanone, the photoinitiator and the compound (Formula 7) or commercially available reactive acrylate were blended. And then the solution was filtered with a Teflon membrane filter to remove fine particles having a size of 0.2 μm or more. Thereafter, the filtered solution is spin-coated onto various types of substrates, preferably, a silicon wafer substrate, and then subjected to a UV curing by the use of a UV irradiating apparatus in a nitrogen atmosphere, thereby obtaining a desired thin film.

Preferably, the coating mixture comprises 30–70 wt % of the fluorine compound selected from the group consisting of fluorine compounds of Formula 1, 30–70 wt % of acrylate selected from the group consisting of acrylate compounds of Formula 7 or 8, and 0.5–4 wt % of the photoinitiator.

The optical waveguide device using the fluorine compound includes a lower cladding layer, a core layer and an upper cladding layer, laminated sequentially on a planar substrate. In such a case, the core layer and the upper and lower cladding layers are formed of the fluorine compound.

As for the fabrication of the optical waveguide device, examples of the substrate for use in the polymer device include polymer plate, glass, silica plate and so on. Preferably, a silicon wafer substrate is used. As a lower cladding, a silica layer is formed or a polymer material having a refractive index lower than that of a polymer constituting a core layer is coated on such a substrate and cured. The formation of a thin film accords to the above manner. An optical waveguide core material is coated on the lower cladding layer and cured, after which a photolithographic process is performed to form optical waveguide patterns. Using a reactive ion etching (RIE) process or an inductive coupled plasma (ICP) etching process, the core layer are etched. Finally, a polymer material for an upper cladding layer is coated on the core layer and cured. Thusly fabricated optical device is diced and polished, thus forming an end face of the device for input and output of light waves.

The fluorine compound having perfluorostyrene introduced at a terminal thereof has higher fluorine content, compared to acrylate compounds. Hence, inherent light absorption of the compound by vibrations of C—H bonds is prevented, thus lowering the optical loss in optical communication wavelength. In addition, the optical birefringence is very low, and thus the fabrication of the optical device with low polarization dependence becomes facile (Table 1). Further since the inventive fluorine compound has no polar functional groups, the moisture absorption is low. Referring to FIG. 1, it can be seen that the mixture of fluorine compounds of the present invention has an influence on the control of the refractive index. By a UV curing or a thermal curing, a thin film can be easily formed, thus fabricating the optical waveguide device having excellent thermal stability and chemical resistance.

Having generally described this invention, a further understanding can be obtained by reference to specific examples which are provided herein for the purpose of illustration only and are not intended to be limiting unless otherwise specified.

EXAMPLE 1

Preparation of Compound having Repeat Unit Represented by Formula A 3.0 g (16.12 mmol) of hexafluorobenzene and 5.17 g (19.70 mmol) of 2,2,3,3,4,4,5,5-octafluoro-1,6-hexanediol were placed into a 100 mL three-neck flask, to which 46 mL of a DMAc solvent was added to completely dissolve the reactants in the flask. 2.05 g of NaOH was further added into the flask, after which the resulting mixture was stirred at room temperature for 24 hours in a nitrogen atmosphere. Then, the reaction mixture was added with 1.39 g (7.16 mmol) of pentafluorostyrene and stirred for more 12 hours. Thusly obtained reaction mixture was extracted with deionized water and ether. The extracted ether layer was dried with magnesium sulfate, and ether was evaporated by a rotary evaporator. The produced liquid compound with very high viscosity was dried at room temperature using a vacuum pump to remove the residual solvent. 1H-NMR (Acetone $d_6$) δ 4.90 (m), 5.75 (d of d), 6.04 (d of, d), 6.68 (d of d). Mn=2,560 (NMR).

EXAMPLE 2

Preparation of Compound having Repeat Unit Represented by Formula B

The present example was performed in the same manner as in example 1, with the exception being that 4.87 g (19.70 mmol) of bromopentafluorobenzene was used, instead of hexafluorobenzene. 1H-NMR (Acetone $d_6$). δ 4.92 (m), 5.73 (d of d), 6.04 (d of d), 6.67 (d of d). Mn=2,900 (NMR).

EXAMPLE 3

Preparation of Compound having Repeat Unit Represented by Formula C 2.26 g (12.15 mmol) of hexafluorobenzene and 6.09 g (14.85 mmol) of perfluorotetraethylene glycol were placed into a 100 mL three-neck flask, to which 47 mL of a DMAc solvent was added to completely dissolve the reactants in the flask. 1.54 g of NaOH was further added into the flask, after which the resulting mixture was stirred at room temperature for 24 hours in a nitrogen atmosphere. Then, the reaction mixture was added with 1.05 g (5.40 mmol) of pentafluorostyrene and stirred for 12 hours. Thusly obtained reaction mixture was extracted with deionized water and ether. The extracted ether layer was dried with magnesium sulfate, and ether was evaporated by a rotary evaporator. The produced liquid compound was dried at room temperature using a vacuum pump. 1H-NMR (CDCl$_3$). δ 4.48 (m), 5.66 (d of d), 6.03 (d of d), 6.59 (d of d). Mn=3,150 (NMR).

EXAMPLE 4

Preparation of Compound having Repeat Unit Represented by Formula D

The present example was performed in the same manner as in example 3, with the exception being that 3.0 g (12.15 mmol) of bromopentafluorobenzene was used, instead of hexafluorobenzene. 1H-NMR (Acetone $d_6$): δ 4.50 (m), 5.65 (d of d), 6.03 (d of d), 6.60 (d of d). Mn=3,470 (NMR)

EXAMPLE 5

Preparation of Compound having Repeat Unit Represented by Formula E 3.0 g (16.12 mmol) of hexafluorobenzene and 6.62 g (19.70 mmol) of 2,2-bis (4-hydroxyphenyl)hexafluoropropane were placed into a 100 mL three-neck flask, to which 55 mL of a DMAc solvent was added to completely dissolve the reactants in the flask. 2.05 g of NaOH was further added into the flask, after which the resulting mixture was stirred at room temperature for 24 hours in a nitrogen atmosphere. Then, 1.39 g (7.16 mmol) of pentafluorostyrene was added to the reaction mixture, which was then stirred for 12 hours. The reaction mixture was extracted with deionized water and ether. The extracted ether layer was dehydrated with magnesium sulfate, and ether was evaporated by a rotary evaporator. The produced white solid compound was dried at 30° C. in a vacuum oven. 1H-NMR (Acetone $d_6$): δ 5.80 (d of d), 6.09 (d of d), 6.74 (d of d), 7.26 (d), 7.43 (d). Mn=2,980 (NMR).

EXAMPLE 6

Preparation of Compound having Repeat Unit Represented by Formula F

In a 100 mL three-neck flask, 5.0 g (14.97 mmol) of decafluorobiphenyl and 6.15 g (18.29 mmol) of 2,2-bis(4-hydroxyphenyl)hexafluoropropane were completely dissolved in 63 mL of a DMAc solvent. Then, 1.90 g of NaOH was further added into the flask, after which the resulting mixture was stirred at room temperature for 24 hours in a nitrogen atmosphere. To this reaction 1.29 g (6.64 mmol) of pentafluorostyrene was added and stirred for 12 hours. The reaction mixture was extracted with deionized water and ether. The extracted ether layer was dehydrated with magnesium sulfate, and ether was evaporated by a rotary evaporator. The produced white solid compound was dried at 30° C. in a vacuum oven. 1H-NMR (Acetone $d_6$): δ 5.82 (d of d), 6.11 (d of d), 6.75 (d of d), 7.30 (d), 7.43 (d). Mn=3,610 (NMR).

EXAMPLE 7

Preparation of Compound Represented by Formula Aa

In a 100 mL three-neck flask, 5.0 g (13.81 mmol) of 2,2,3,3,4,4,5,5,6,6,7,7-dodecafluoro-1,8-octanediol and 5.36 g (27.62 mmol) of pentafluorostyrene were completely dissolved in 59 mL of a DMAc solvent. 1.44 g of NaOH was further added into the flask. The resulting mixture was stirred at room temperature for 10 hours in a nitrogen atmosphere. Thusly obtained reaction mixture was cooled and then extracted with deionized water and ether. The extracted ether layer was dehydrated with magnesium sulfate, and ether was evaporated by a rotary evaporator. The produced white solid compound was dried at 30° C. in a vacuum oven. 1H-NMR (CDCl$_3$): δ 4.48 (t, 4H) 5.67 (d of d, 2H), 6.05 (d of d, 2H), 6.61 (d of d, 2H).

EXAMPLE 8

Preparation of Compound having Repeat Unit Represented by Formula Ac

The present example was performed in the same manner as in example 7, with the exception being that 5.66 g (13.81 mmol) of perfluorotetraethylene glycol was used, instead of 2,2,3,3,4,4,5,5,6,6,7,7-dodecafluoro-1,8-octanediol. 1H-NMR (CDCl$_3$): δ 4.64 (t, 4H), 5.66 (d of d, 2H), 6.05 (d of d, 2H), 6.60 (d of d, 2H).

EXAMPLE 9

Preparation of Compound Represented by Formula Ab 5.0 g (14.87 mmol) of 2,2-bis(4-hydroxyphenyl)hexafluoropropane and 5.77 g (27.74 mmol) of pentafluorostyrene were placed into a 100 mL three-neck flask, to which 61 mL of a DMAc solvent was added to completely dissolve the reactants in the flask. 1.55 g of NaOH was further added into the flask, after which the resulting mixture was stirred at room temperature for 12 hours in a nitrogen atmosphere. Then, the reaction mixture was cooled and extracted with deionized water and ether. The extracted ether layer was dehydrated with magnesium sulfate, and ether was evaporated by a rotary evaporator. Finally, the produced white solid compound was dried at 30° C. in a vacuum oven. 1H-NMR (Acetone $d_6$): δ 5.81 (d of d, 2H), 6.10 (d of d, 2H), 6.74 (d of d, 2H), 7.25 (d, 4H), 7.44 (d, 4H).

EXAMPLE 10

Preparation of Compound Represented by Formula Ad 5.0 g (14.27 mmol) of 9,9-bis (4-hydroxyphenyl) fluorene and 5.54 g (28.54 mmol) of pentafluorostyrene were placed into a 100 mL three-neck flask, and then completely dissolved with 60 mL of a DMAc solvent. 1.48 g of NaOH was further added into the flask. The resulting mixture was stirred at room temperature for 8 hours in a nitrogen atmosphere. Then, the reaction mixture was cooled and extracted with deionized water and ether. The extracted ether layer was dehydrated with magnesium sulfate, and ether was evaporated by a rotary evaporator. Finally, the produced white solid compound was dried at 30° C. in a vacuum oven. 1H-NHR (Acetone $d_6$): δ 5.77 (d of d, 2H), 6.07 (d of d, 2H), 6.70 (d of d, 2H), 7.00 (d, 4H), 7.20 (d, 4H), 7.33 (t, 2H), 7.39 (t, 2H), 7.46(d, 2H), 7.88 (d, 2H).

EXAMPLE 11

Preparation of Compound Represented by Formula Ba

Into a 100 mL three-neck flask, 3.0 g (9.79 mmol) of 1,1,1-tris(4-hydroxyphenyl)ethane and 5.70 g (29.38 mmol) of pentafluorostyrene were placed and then completely dissolved with 49 mL of a DMAc solvent. 1.57 g of NaOH was further added into the flask. The resulting mixture was stirred at room temperature for 8 hours in a nitrogen atmosphere, after which the reaction mixture was extracted with deionized water and ether. The extracted ether layer was dehydrated with magnesium sulfate, and ether was evaporated by a rotary evaporator. The produced white solid compound was dried at 30° C. in a vacuum oven. 1H-NMR (Acetone $d_6$): δ 2.16 (s, 3H), 5.78 (d of d, 3H), 6.08 (d of d, 3H), 6.73 (d of d, 3H), 7.04 (d, 6H), 7.10 (d, 6H).

EXAMPLE 12

Preparation of Compound Having Repeat Unit Represented by Formula Bb

The present example was performed in the same manner as in example 11, with the exception being that 1.23 g (9.79 mmol) of 1,2,4-benzenetriol was used, instead of 1,1,1-tris (4-hydroxyphenyl)ethane. 1H-NMR (Acetone $d_6$): δ 5.3 (d of d, 3H), 5.4 (d of d, 3H), 6.3 (S, 3H), 6.9 (d of d, 3H).

EXAMPLE 13

Preparation of Compound Represented by Formula Cb

In a 100 mL three-neck flask, 5.0 g (13.81 mmol) of 2,2,3,3,4,4,5,5,6,6,7,7-dodecafluoro-1,8-octanediol was completely dissolved in 80 mL of a DMAC solvent. 3 g of triethylamine was further added into the flask. While a reactor was maintained at 0° C. or lower in a nitrogen atmosphere, acryloyl chloride was droplets slowly added to the reaction in the reactor, after which the reaction mixture was stirred for 3 hours. The reaction mixture was filtered to remove a formed ammonium salt, and extracted with deionized water and ether. The extracted ether layer was dehydrated with magnesium sulfate, and ether was evaporated by a rotary evaporator. The produced liquid compound was vacuum distilled to produce a pure compound. 1H-NMR ($CDCl_3$) d 4.66 (t, 4H), 5.99 (d, 2H), 6.22 (q, 2H), 6.54 (d, 2H).

EXAMPLE 14

Preparation of Polymer Coating Solution Including Perfluorostyrene Compound Represented by Formula 1 or 2

Each fluorine compound having perfluorostyrene introduced at a terminal thereof, prepared in examples 1–12, was admixed with Irgacure 651 as a photoinitiator, and then dissolved in 10–100 wt % of PGMEA or cyclohexanone solvent, depending on viscosity. The solution was further mixed with a compound represented by Formula 5 and 10–60 wt % of reactive acrylate, to produce a coating solution, which was then filtered with a 0.2 μm Teflon filter. Thereby, a coating solution suitable for use in the core and cladding layers as thin films of an optical waveguide device was produced. The following Table 1 shows the refractive index and the optical loss of thin films formed after being cured, depending on the composition and the content of the composition.

TABLE 1

| Exp. No. | Composition | Content (wt %) | Refractive index | Light Loss (dB/cm) |
|---|---|---|---|---|
| 1 | Compound (B) | 70 | 1.4540 | 0.16 |
|  | Photoinitiator (Irgacure 651) | 1 |  |  |
|  | Solvent (PGMEA) | 29 |  |  |
| 2 | Compound (C) | 70 | 1.3910 | 0.15 |
|  | Photoinitiator (Irgacure 651) | 1 |  |  |
|  | Solvent (PGMEA) | 29 |  |  |
| 3 | Compound (D) | 70 | 1.4110 | 0.17 |
|  | Photoinitiator (Irgacure 651) | 1 |  |  |
|  | Solvent (PGMEA) | 29 |  |  |
| 4 | Compound (F) | 40 | 1.4930 | 0.21 |
|  | Photoinitiator (Irgacure 651) | 1 |  |  |
|  | Solvent (PGMEA) | 59 |  |  |
| 5 | Compound (B) | 40 | 1.4790 | 0.3 |
|  | Compound (Ba) | 15 |  |  |
|  | Photoinitiator (Irgacure 651) | 1 |  |  |
|  | Solvent (cyclohexanone) | 44 |  |  |
| 6 | Compound (B) | 40 | 1.4450 | 0.34 |
|  | Compound (Cb) | 30 |  |  |
|  | Compound (Cc) | 10 |  |  |
|  | Pentaerythrol triacrylate | 19 |  |  |
|  | Photoinitiator (Irgacure 651) | 1 |  |  |
| 7 | Compound (B) | 40 | 1.4320 | 0.31 |
|  | Compound (Cb) | 25 |  |  |
|  | Compound (Cc) | 25 |  |  |
|  | Pentaerythrol triacrylate | 9 |  |  |
|  | Photoinitiator (Irgacure 651) | 1 |  |  |

In Table 1, the refractive index was measured by a prism coupler, and the optical loss was determined by the incorporation of a slab waveguide using an index matching oil. The refractive index and the optical loss were measured at a wavelength of 1550 nm.

EXAMPLE 15

Precise Control of Refractive Index

In an optical waveguide device, precise control of refractive index is needed between the core and cladding layers in order to contain the single mode condition. For this, the coating solutions, having different refractive indexes as shown in example 14, were mixed together by a weight ratio. FIG. 2 shows the relationship between the refractive index and the coating solution mixture obtained by mixing the coating solutions shown in experimental numbers 6 and 7 of Table 1 in example 14.

EXAMPLE 16

Preparation of Polymer Thin Film using Polymer Coating Solution Containing Perfluorostyrene Compound Represented by Formula 1 or 2

The polymer coating solution having perfluorostyrene, prepared in example 14, was filtered with a 0.2 μm Teflon filter. Of various types of substrates, a silicon wafer substrate was preferably used. Such a substrate was spin-coated with the filtered polymer coating solution at 500–5000 rpm, and cured under a UV light intensity of 5–200 mW/cm$^2$, preferably 10–50 mW/cm$^2$, using a mercury lamp in a nitrogen atmosphere for 2–30 min, and then post baked on a hot plate at 100–200° C. for 0.5–1 hour, to prepare a desired polymer thin film. The obtained thin film is superior in chemical resistance, thus realizing a facile fabrication of an optical device having multi-layered thin films.

EXAMPLE 17

Fabrication of Optical Device Using Polymer

As a substrate suitable for use in the fabrication of an optical device, a silicon wafer was used. As a lower cladding of the optical device, a silica layer was formed or the inventive polymer having a refractive index lower by about 0.3–1% than that of a core layer polymer was coated on the silicon wafer substrate, and then cured. The formation of the thin film was performed in the same manner as in example 16. A polymer core material was coated on the lower cladding layer and then cured, after which a photomask was aligned and a photolithographic process was performed, thereby forming optical waveguide patterns. Then, by the use of a reactive ion etching process or an inductive coupled plasma process, the core layer of the optical waveguide, were etched. Finally, the same polymer material as the coating solution used for the lower cladding layer was coated on the core layer and then cured, to obtain an upper cladding layer. Thereby, a desired optical waveguide device was fabricated. As necessary, a drive electrode forming process might be further performed for driving an optical device on the upper cladding layer. The fabricated optical device wafer was diced and polished by the use of a saw and a polisher, thereby forming an end face of the device for input and output of light waves.

As described above, the present invention provides a fluorine compound having perfluorostyrene introduced at a terminal thereof, and a coating solution and an optical waveguide device using such a fluorine compound. The fluorine compound has high fluorine content on a molecular structure thereof, whereby inherent light absorption due to molecular vibrations can be prevented in optical communication wavelength, thus decreasing optical loss.

Further, the optical birefringence of the thin film, which is attributed to a molecular structure of the film material, is remarkably reduced, and thus the optical device with low polarization dependence can be easily fabricated. Moreover, the fluorine compounds are mixed together, thereby achieving precise control of the refractive index. In addition, the fluorine compound has no polar functional groups, resulting in low moisture absorption. By a UV curing or a thermal curing, the thin film can be readily formed, thus obtaining an optical waveguide device having excellent thermal stability and chemical resistance.

The present invention has been described in an illustrative manner, and it should be understood that the terminology used is intended to be in the nature of description rather than of limitations. Many modifications and variations of the present invention are possible in light of the above teachings. Therefore, it should be understood that within the scope of the appended claims, the invention may be practiced otherwise than as specifically described.

What is claimed is:

1. A fluorine compound having perfluorostyrene introduced at a terminal thereof, as represented in the following Formula 1:

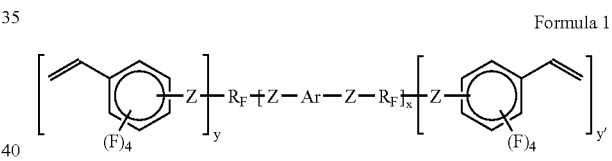

Formula 1 wherein Z is O or S; $R_F$ is —CH$_2$(CF$_2$)$_n$CH$_2$—, CH$_2$CF$_2$O(CF$_2$CF$_2$O)$_n$CF$_2$CH$_2$—, or

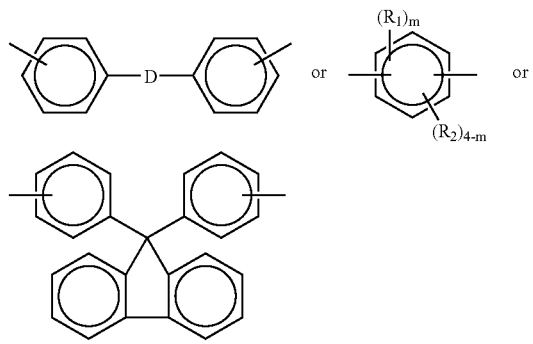

wherein n is a natural number of 1–12; D is selected from the group consisting of —C(CF$_3$)$_2$—, —C(CH$_3$)$_2$—, —CO—, —SO$_2$—, —O— and —S—; R$_1$ and R$_2$ are independently selected from the group consisting of H, or halogen elements, including F, Cl, Br and I; and m is a natural number of 1–3; y and y' are 1; x is an integer of 1–200; and Ar = 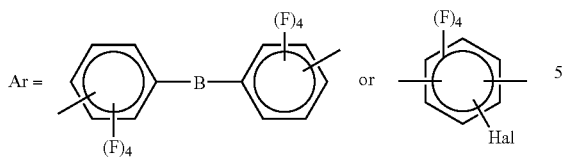

wherein B is a single bond or selected from the group consisting of —CO—, —SO$_2$—, —S— and —O—; and Hal is selected from the group consisting of F, Cl, Br and I.

2. The fluorine compound as defined in claim 1, wherein Z is O, and x is an integer of 2–50.

3. The fluorine compound as defined in claim 1, wherein Ar is halogenated pentafluorobenzene, and R$_F$ is CH$_2$(CF$_2$)$_n$CH$_2$—, —CH$_2$CF$_2$(OCF$_2$CF$_2$)$_n$ OCF$_2$CH$_2$— or

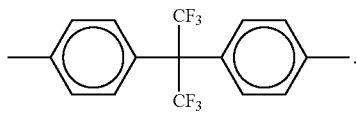

4. A polymer coating solution, comprising at least one fluorine compound selected from the group consisting of fluorine compounds having perfluorostyrene introduced at a terminal thereof of claim 1, at least one acrylate compound selected from the group consisting of acrylate compounds represented by the following Formula 7, and a photoinitiator:

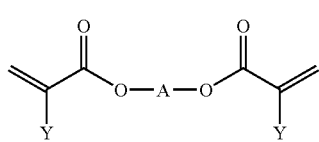

Formula 7 wherein A is a fluorinated aliphatic or aromatic group, and Y is H or CH$_3$.

5. The polymer coating solution as defined in claim 4, wherein A is —CH$_2$(CF$_2$)$_n$CH$_2$—, —CH$_2$CF$_2$(OCF$_2$CF$_2$)$_n$ OCF$_2$CH$_2$— or

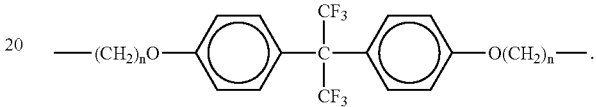

6. An optical waveguide device, comprising a lower cladding layer formed on a planar substrate, a core layer formed on the lower cladding layer, and an upper cladding layer formed on the core layer, wherein the core layer and the lower and upper cladding layers include the fluorine compound of claim 1.

* * * * *

UNITED STATES PATENT AND TRADEMARK OFFICE
CERTIFICATE OF CORRECTION

| | | |
|---|---|---|
| PATENT NO. | : 7,202,324 B2 | Page 1 of 1 |
| APPLICATION NO. | : 11/034646 | |
| DATED | : April 10, 2007 | |
| INVENTOR(S) | : Kim et al. | |

It is certified that error appears in the above-identified patent and that said Letters Patent is hereby corrected as shown below:

<u>Column 17</u>, line 17, Claim 3, "$CH_2$" should read -- —$CH_2$ --

Signed and Sealed this

Eighteenth Day of September, 2007

JON W. DUDAS
*Director of the United States Patent and Trademark Office*